United States Patent
Lindsey et al.

(10) Patent No.: US 6,776,961 B2
(45) Date of Patent: Aug. 17, 2004

(54) WORKSTATION FOR INTEGRATING AUTOMATED CHEMICAL ANALYZERS

(75) Inventors: Christopher W. Lindsey, Aliso Viejo, CA (US); George K. Shibata, Upland, CA (US); Songtai Tu, Yorba Linda, CA (US); Steven D. Mack, Mira Loma, CA (US); Dang M. Ngo, Fountain Valley, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 390 days.

(21) Appl. No.: 09/911,600

(22) Filed: Jul. 23, 2001

(65) Prior Publication Data

US 2002/0015665 A1 Feb. 7, 2002

Related U.S. Application Data

(63) Continuation-in-part of application No. 09/620,835, filed on Jul. 21, 2000, now abandoned.

(51) Int. Cl.$^7$ .............................................. G01N 35/02
(52) U.S. Cl. ............................ 422/63; 422/65; 422/64; 422/100; 436/43; 436/47; 436/48
(58) Field of Search ............................ 422/63, 64, 65, 422/67, 100, 102, 104; 436/43, 47, 48, 807

(56) References Cited

U.S. PATENT DOCUMENTS 5,380,488 A  1/1995 Wakatake
5,575,976 A  * 11/1996 Choperena et al. ........... 422/64
5,833,925 A  11/1998 Shu et al.
5,863,506 A  1/1999 Farren ......................... 422/102

FOREIGN PATENT DOCUMENTS

JP         0 977 039 A2    2/2000

* cited by examiner

Primary Examiner—Lyle A. Alexander
(74) Attorney, Agent, or Firm—Hogan & Hartson, LLP

(57) ABSTRACT

A workstation for integrating two or more automated analyzers. The workstation includes a sample rack handler assembly, having a single common sample rack input area for loading sample racks for the two or more automated analyzers, and a sample rack bypass area for passing sample racks to be processed by one of the two or more automated analyzers. The workstation also includes a sample aliquoting assembly, having a sample pipetter station for aliquoting samples into aliquot vessels for processing by another one of the two or more automated analyzers. The workstation further includes an internal shuttle for shuttling the sample racks between the sample rack input area, the sample rack bypass area, and the sample pipetter station, and an external shuttle for shuttling the sample racks between the sample rack input area, the sample rack bypass area, and the one of the two or more automated analyzers. In addition, the workstation includes a pick-and-place mechanism for transporting the aliquot vessels between the sample pipetter station and the other one of the two or more automated analyzers. A single common control console is provided for the workstation and the two or more automated analyzers.

26 Claims, 5 Drawing Sheets

WORKSTATION FOR INTEGRATING AUTOMATED CHEMICAL ANALYZERS

This application is a continuation-in-part application of application Ser. No. 09/620,835, filed Jun. 21, 2000 abandoned, which application is hereby incorporated by reference in its entirety.

BACKGROUND OF THE INVENTION

1. Area of the Art

The invention relates generally to automated chemical analyzers, and specifically to workstations for integrating automated chemical analyzers.

2. Description of the Prior Art

Automated chemical analyzers are commonly used in clinical chemistry sampling and analyzing applications. Automated analytical equipment, such as automated analytical chemistry workstations, can efficiently perform clinical analysis on a large number of samples, with tests being run concurrently or within short time intervals. Efficiencies result in part because of the use of automated sample identification and tracking. This equipment can automatically prepare appropriate volume samples and can automatically set the test conditions needed to perform the scheduled tests. Test conditions can be independently established and tracked for different testing protocols simultaneously in progress within a single test station, facilitating the simultaneous execution of a number of different tests based on different chemistries and requiring different reaction conditions. Automated analytical equipment is particularly well-suited for high volume testing environments, such as those existing in many hospitals and in centralized testing laboratories, because the automatic sample handling allows for more precise sample identification and sample tracking. Automatic handling and tracking of samples significantly reduces the opportunity for human error or accidents that can lead to either erroneous test results or undesirable contamination.

An example of such an automated clinical chemistry system is provided by U.S. Pat. No. 5,575,976 to Choperena, et al., which describes embodiments of the Access® Special Chemistry Analyzer presently available through the Clinical Chemistry Division of Beckman Coulter, Inc., located in Brea, Calif. Another automated chemistry analyzer is the SYNCHRON LX®20 General Chemistry Analyzer, as described in U.S. Pat. No. 5,863,506 to Farren, U.S. Pat. No. 5,833,925 to Hsu, et al., and in U.S. patent application Ser. No. 08/748,135 to Robins, et al., entitled "Pressure Detector for Chemical Analyzers," and in U.S. patent application Ser. No. 08/746,649 to Fechtner, et al., "Automatic Chemistry Analyzer with Sample Cup Piercing Assembly," which is also presently available through the Clinical Chemistry Division of Beckman Coulter, Inc., located in Brea, Calif. These chemistry systems can provide automated analysis of a number of samples.

In many situations, there is a need to perform a series of analysis by various different analyzers. For example, it is often required that a general chemical analysis be performed and then followed by a more specific immunodiagnostic analysis. In addition, reflex testing of a sample is often needed for a particular analysis.

Therefore, it is desirable to provide a workstation for integrating two or more automated chemical analyzers for performing a series of chemical analysis and having the capacity of facilitating reflex testing.

SUMMARY OF THE INVENTION

It is an object of the present invention to provide a workstation for integrating two or more automated chemical analyzers.

It is also an object of the present invention to provide a workstation for integrating two or more automated chemical analyzers where the automated chemical analyzers will have a single common sample input area.

It is another object of the present invention to provide a workstation for integrating two or more automated chemical analyzers where the automated chemical analyzers will have a single common control console.

It is an additional object of the present invention to provide a workstation for integrating two or more automated chemical analyzers that can facilitate automated reflex testing from one automated chemical analyzer to another.

It is still an object of the present invention to provide a workstation for integrating two or more automated chemical analyzers with the function of sampling from closed sample tubes.

It is a further object of the present invention to provide a workstation for integrating two or more automated chemical analyzers with the capacity of rapid loading of STAT samples.

The objects and advantages of the present invention are achieved in a workstation for two or more automated analyzers of the present invention. The workstation of the present invention includes a sample rack handler assembly having a single common sample rack input area for loading sample racks for one of the two or more automated analyzers, a sample rack bypass area for passing sample racks to be processed by the one of the two or more automated analyzers, and a sample rack output area for off-loading sample racks after being processed by the one of the two or more automated analyzers.

The workstation of the present invention also includes a sample aliquoting assembly having a cap-piercing station for piercing caps of closed sample tubes contained in the sample racks, and a sample pipetter station for pipetting sample aliquot and dispensing the sample aliquot to aliquot vessels for processing by another one of the two or more automated analyzers.

The workstation of the present invention further includes an internal shuttle for shuttling the sample racks between the sample rack input area, the sample rack bypass area, the cap-piercing station and the sample pipetter station, and an external shuttle for shuttling the sample racks between the sample rack input area, the sample rack bypass area, and the one of the two or more automated analyzers.

The workstation of the present invention additionally includes a pick-and-place mechanism for transporting the aliquot vessels between the sample pipetter station and the other one of the two or more automated analyzers.

Such an arrangement has been found to provide a number of advantages. As explained in greater detail below, the workstation of the present invention integrates two or more automated chemical analyzers for performing a series of chemical analysis. The workstation of the present invention also provides a single common sample input area and a single control console for the integrated automated chemical analyzers. In addition, the workstation of the present invention can facilitate automated reflex testing from one automated chemical analyzer to another. Furthermore, the workstation of the present invention has the function of sampling from closed sample tubes and the capacity for rapid loading of STAT samples.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawing(s). The(se) drawing(s) depict(s) only a typical embodiment of the invention and do not therefore limit its scope. The drawing(s) serve(s) to add specificity and detail, in which.

DETAILED DESCRIPTION OF THE INVENTION

The present invention is directed to a new and unique workstation for integrating two or more automated chemical analyzers. In accordance with embodiments of the present invention, the workstation of the present invention includes a sample rack handler assembly and a sample aliquoting assembly.

The sample rack handler assembly has a single common sample rack input area for loading sample racks for the two or more automated analyzers, a sample rack bypass area for passing sample racks to be processed by one of the two or more automated analyzers, and a sample rack output area for off-loading sample racks after being processed by the one of the two or more automated analyzers. This sample rack handler assembly provides the workstation of the present invention a single common sample input area for the integrated automated chemical analyzers.

The sample aliquoting assembly has a cap-piercing station for piercing caps of closed sample tubes contained in the sample racks, and a sample pipetter station for pipetting sample aliquot and dispensing the sample aliquot to aliquot vessels for processing by one of the two automated analyzers. This sample aliquoting assembly of the workstation allows closed tube sampling on the combined automated analyzers.

The workstation also includes an internal shuttle for shuttling the sample racks to be processed by the one of the two automated analyzers from the sample rack input area to the sample rack bypass area, and also for shuttling the sample racks to be aliquoted from the sample rack input area to the sample pipetter station, and, further, for shuttling sample racks to and from the cap piercing station.

The workstation further includes an external shuttle for shuttling the sample racks to be processed by the one of the two automated analyzers from the sample rack bypass area to the one of the two automated analyzers, and also for shuttling the sample racks from the one of the two automated analyzers back to the sample rack output area after being processed by the one of the two automated analyzers.

The workstation additionally includes a pick-and-place mechanism for transporting the aliquot vessels between the sample pipetter station and the other one of the two automated analyzers.

The workstation further includes a common computerized control system for controlling the workstation and the two or more analyzers integrated by the workstation. The control system is electrically and electronically coupled to the control electronics of the workstation and the analyzers, so that various tasks can be performed, including but not limited to, sample programming, reagent load control, system setup and status, maintenance and diagnostics. The workstation of the present invention allows automatic reflex testing from one analyzer to the other.

Figure 1:
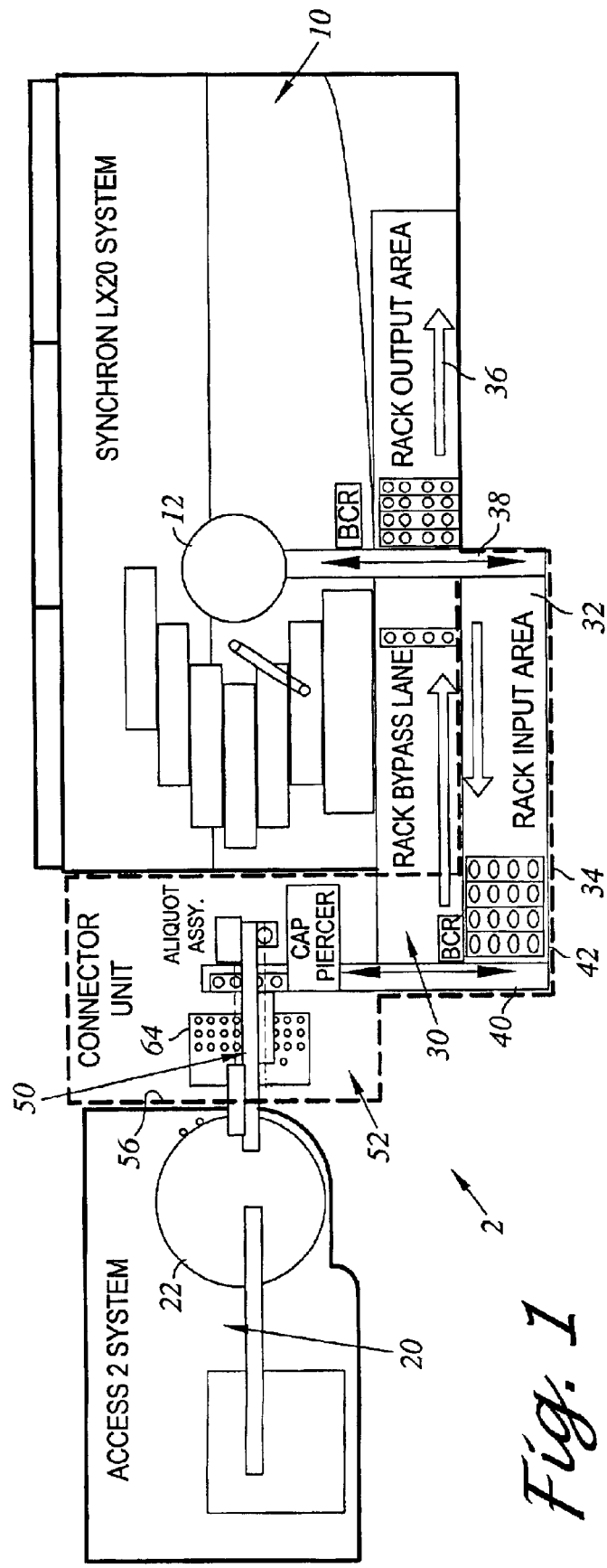
FIG. 1 is an illustrative block diagram showing two automated analyzers integrated by a preferred embodiment of the workstation of the present invention.
Figure 2:
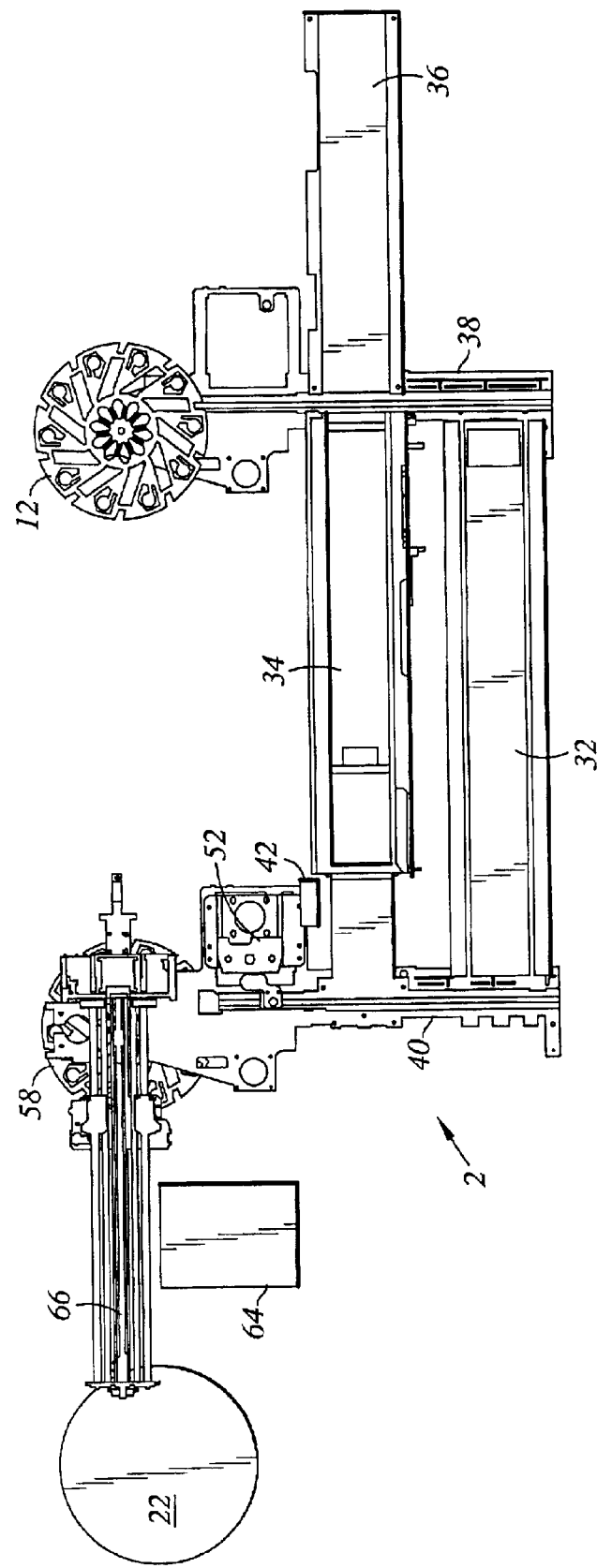
FIG. 2 is an illustrative top view showing the layout of the preferred embodiment of the workstation present invention.

Having thus provided an overview of certain embodiments of the present invention, this specification now provides a more detailed discussion of preferred embodiments of the present invention with particular reference to the drawings. Referring to FIGS. 1 and 2, there is shown at workstation 2 a workstation of the present invention for integrating, for example, an automated general chemical analyzer 10, such as a Synchron LX 20 General Chemistry System, and an automated immunodiagnostic analyzer 20, such as an Access 2 Heterogeneous Immunochemistry System, both manufactured by and available from Beckman Coulter, Inc., the Assignee of this patent application. It should be understood that the workstation of the present invention may also be used for integrating other types of automated chemical or immunochemistry analyzers, and the integration of the analyzers is within the skill of the art in view of the present disclosure.

Typically, the automated general chemical analyzer 10 has, among other components, a sample wheel 12 for receiving input sample racks for general chemical analysis. Similarly, the automated immunodiagnostic analyzer 20 also has, among other components, a sample wheel 22 for receiving input sample containers for immunodiagnostic analysis.

The workstation 2 of the present invention has the following main components: a computer console, a sample rack handler assembly 30, and a sample aliquot assembly 50.

Figure 3:
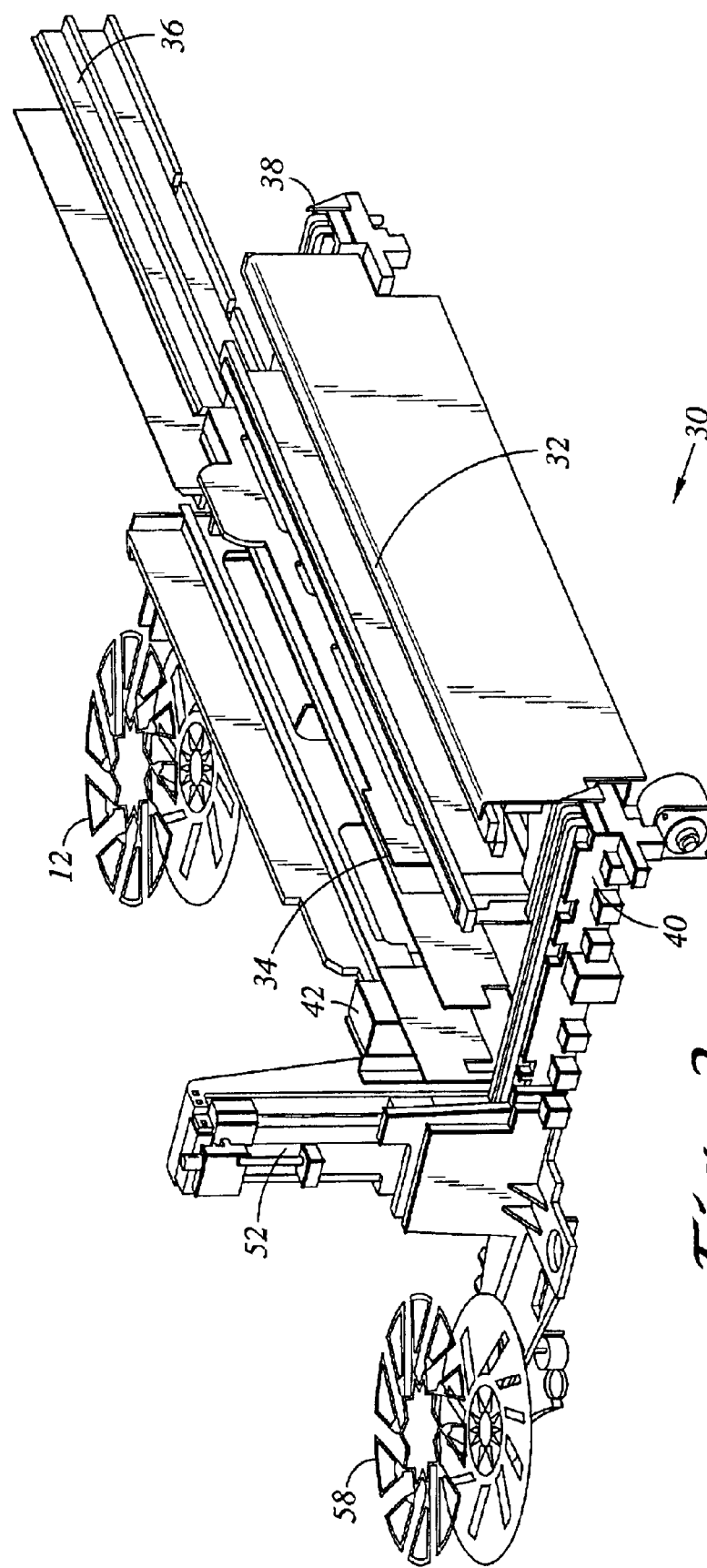
FIG. 3 is an illustrative perspective view of a sample rack handler assembly of the workstation of the present invention.

Referring to FIGS. 1, 2 and 3, there is shown the sample rack handler assembly 30 of the workstation 2 of the present invention. The sample rack handler assembly 30 provides a single point of sample entry for the entire integrated system. It has the following main component parts: an input area 32, a bypass area 34, an output area 36, an external shuttle 38, an internal shuttle 40, and a bar code reader (BCR) 42.

The input area 32 provides a sample rack input path for the workstation 2. The bypass area 34 provides a sample rack path from the workstation 2 to the general chemical analyzer 10. The output area 36 provides a sample rack output path.

The external shuttle 38 shuttles the sample racks from the bypass area 34 to the sample wheel 12 of the general chemical analyzer 10, and also shuttles the sample racks back from the sample wheel 12 of the general chemical analyzer 10 to the output area 36, or to the input area 32, if reflex testing is required. The internal shuttle 40 shuttles sample racks from the input area 32 to the bypass area 34, and also shuttles sample racks further to the sample aliquot assembly 50 of the workstation 2. The structural and functional arrangements of the shuttles 38 and 40 conform to existing arrangements known to those of ordinary skill in the art, and therefore will not be described in detail here.

The bar code reader (BCR) 42 is used to obtain identification of the sample racks. It is electronically coupled to the computer console to provide the sample rack identification and test information to the computer console for sample programming. The structural and functional arrangements of the BCR 42 conform to existing arrangements known to those of ordinary skill in the art, and therefore will not be described in detail here.

Figure 4:
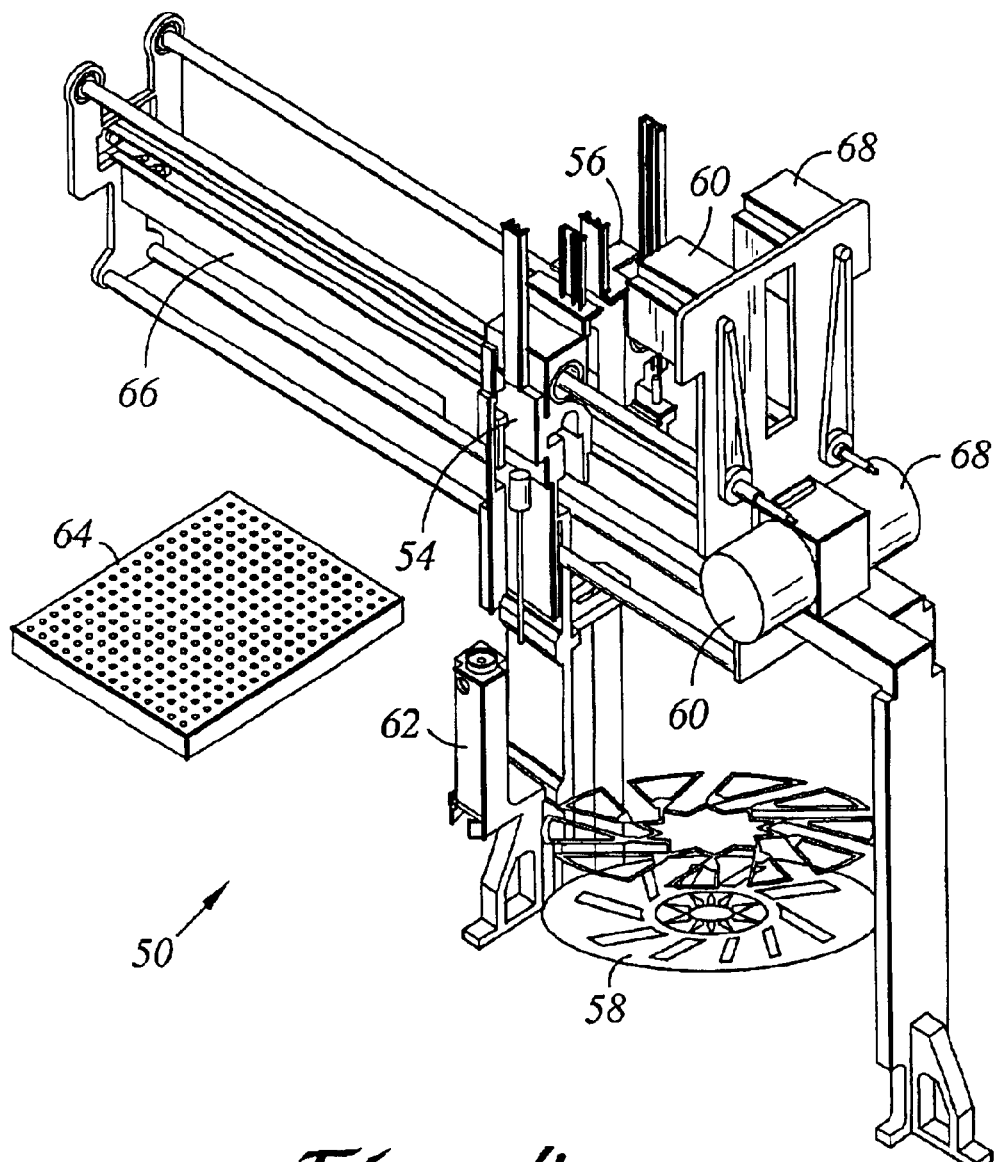
FIG. 4 is an illustrative perspective view of a sample aliquot assembly of the connector unit of the workstation of the present invention.

Referring to FIGS. 1, 2, and 4, there is shown the sample aliquot assembly 50 of the workstation 2 of the present invention. It has the following main component parts: a closed cap-piercing station 52, a sample pipette station 54, a pick-and-place mechanism 56, and an aliquot sample wheel 58.

Sample racks from the sample rack handler assembly 30 are shuttled to the closed cap-piercing station 52 of the sample aliquot assembly 50 by the internal shuttle 40. The closed cap-piercing station 52 is used for piercing the closed caps of sample tubes. A detailed description of the structural and functional arrangements of the closed cap-piercing station is provided in the assignee's co-pending patent application for "Sample Loading and Handling Interface to Multiple Chemistry Analyzers," with Ser. No. 09/335,363. Alternatively, another embodiment of a closed cap-piercing station, described in the assignee's co-pending patent application for "Cap Piercing Station for Closed Container Sampling System," with Ser. No. 09/599,305 may also be used. The contents of the two patent applications are incorporated herein in their entirety by reference.

The sample pipette station 54 is used to aliquot a required amount of sample from a pierced sample tube and then dispense the aliquoted sample into a aliquot vessel positioned on the aliquot vessel storage tray 64. The sample probe carriage is driven by aliquot probe carriage drive motors 60. An aliquot probe wash station 62 is provided for washing the aliquot probe. The structural and functional arrangements of the sample pipette station 54 conform to existing arrangements known to those of ordinary skill in the art, and therefore will not be described in detail here.

The pick-and-place mechanism 56 is used to: (a) transfer aliquot vessels containing aliquoted samples to the sample wheel 22 of the immunodiagnostic analyzer 20; and (b) off-load aliquot vessels from the sample wheel 22 of the immunodiagnostic analyzer 20 to a solid waste container. The pick-and-place mechanism 56 is carried on an assembly gantry 66 and driven by pick-and-place carriage motors 68. A detailed description of the structural and functional arrangements of the pick-and-place mechanism 56 is provided in the assignee's co-pending patent application for "Sample Loading and Handling Interface to Multiple Chemistry Analyzers," with Ser. No. 09/335,363, the contents of which are incorporated herein by reference. Alternative embodiments are also described in the assignee's co-pending patent application for "Method and System for Picking and Placing Reaction Vessels" and are incorporated herein by reference.

Figure 5:
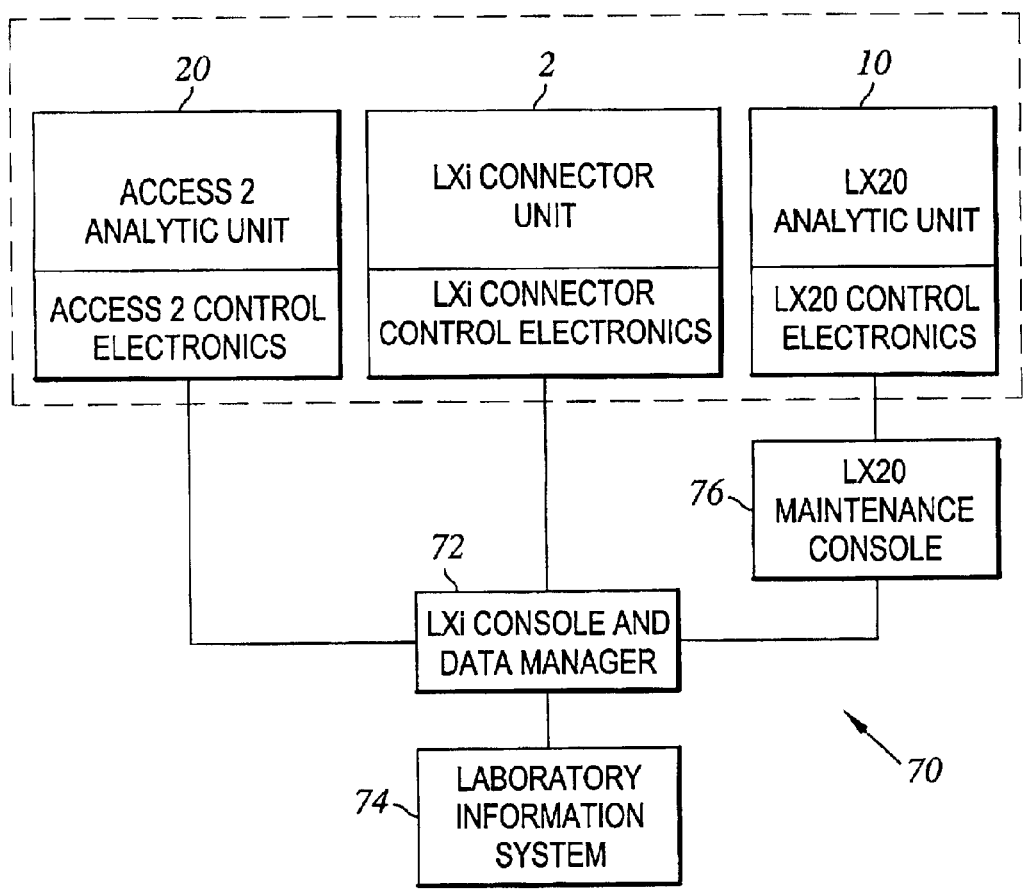
FIG. 5 is an illustrative block diagram showing the common control system of the workstation of the present invention and the integrated automated analyzers.

Referring to FIG. 5, there is shown a common computerized system 70 for controlling the workstation 2 of the present invention, the automated general chemical analyzer 10, and the automated immunodiagnostic analyzer 20, which are integrated by the workstation 2 of the present invention.

The control system 70 utilizes a single common computerized center control console 72 for both the automated general chemical analyzer 10 and the automated immunodiagnostic analyzer 20, as well as for the workstation 2. The computerized center control console 72 is electrically and electronically coupled to the control electronics of the workstation 2 and the two integrated automated analyzers 10 and 20, so that various tasks can be performed, including sample programming, reagent load control, system setup and status, maintenance, and diagnostics.

Optionally, the computerized center control console 72 may be connected to a laboratory information system 74. In addition, a maintenance sub-console 76 may be used for each automated analyzer.

As an example, the control system 70, shown in FIG. 5, includes a sub-console 76 for maintenance of the automated general chemical analyzer 10, in which case the main console 72 and the sub-console 76 are all electrically and electronically coupled to the control electronics of the automated general chemical analyzer 10.

The workstation 2 of the present invention is also constructed for housing facilities for wash solution, air pressure, vacuum for waste handling, power supplies, electronics for monitoring and control of the various modules, and environmental control, as required. The structural and functional arrangements for housing these facilities and of facilities themselves conform to existing arrangements and details known to those of ordinary skill in the art, and therefore will not be described in detail here.

The functions and operations of workstation 2 will be described as follows:

1. Loading Samples to Workstation 2

An operator loads sample racks onto the sample rack input area 32 of the sample rack handler assembly 30. The first sample rack is shuttled from the input area 32 by the internal shuttle 40, passing the bypass area 34, to the BCR 42, where the sample identification, sector number, and tube presence are determined.

Based on this identification information from BCR 42, and data retrieved from the general chemical analyzer 10 and the immunodiagnostic analyzer 20, the computerized control system of the workstation 2 will determine: (a) whether there is a pending analysis to be performed by the immunodiagnostic analyzer 20; and (b) whether the caps or stoppers of the sample tubes in the sample rack have previously been pierced.

If the caps or stoppers of the sample tubes have not been previously pierced, then the sample rack is shuttled to the closed cap-piercing station 52 of the sample aliquot assembly of the workstation 2, where the caps or stoppers of the sample tubes are pierced.

If no analysis is pending at the immunodiagnostic analyzer 20, then the computerized control system of the workstation 2 will ascertain whether the bypass area 34 is full.

If the bypass area 34 is full, then the sample rack will wait until the sample racks already in the bypass area 34 are processed.

If the bypass area 34 is not full, then the sample rack is placed onto the bypass area 34 for processing by the general chemical analyzer 10.

If there is an analysis pending at the immunodiagnostic analyzer 20, then the sample rack is further shuttled to the sample pipette station 54 for sample aliquoting, where a sample aliquot is made. The computerized control system of the workstation 2 will then ascertain whether the bypass area 34 is full.

If the bypass area 34 is full, then the sample rack will wait until the sample racks already in the bypass area 34 are processed.

If the bypass area 34 is not full, then the sample rack is placed onto the bypass area 34 for processing by the general chemical analyzer 10.

This process is repeated until all sample racks have been processed.

2. Sample Aliquoting for Immunodiagnostic Analyzer 20

The sample pipette station 54 of the sample aliquoting assembly 50 of the workstation 2 withdraws a predetermined volume of sample from the sample tube, depending upon the requirements of the immunodiagnostic analyzer 20. The sample pipette station 54 then dispenses the withdrawn sample into an available aliquot vessel.

The aliquoted sample in the aliquot vessel is stored for a predetermined period of time or until there are a predetermined number of aliquot vessels containing aliquoted samples to be analyzed by the immunodiagnostic analyzer 20.

3. Loading Samples to the Immunodiagnostic Analyzer 20

The workstation 2 of the present invention will coordinate the queuing of the samples to be run on the immunodiagnostic analyzer 20. It communicates with the immunodiagnostic analyzer 20 to control the indexing of the sample wheel 22, and transfers sample identification and test information to the immunodiagnostic analyzer 20.

The pick-and-place mechanism 56 of the workstation 2 will load the aliquot vessels containing aliquot from the sample pipette station 54 to the sample wheel 22 of the immunodiagnostic analyzer 20. When all aliquot vessels containing aliquot have been loaded onto the sample wheel 22 of the immunodiagnostic analyzer 20, the test will be initiated.

4. Off-Loading Samples from the Immunodiagnostic Analyzer 20

When all sampling requirements of the aliquoted sample have been completed by the immunodiagnostic analyzer 20, the aliquot vessels containing the completed aliquot sample will be moved from the sample wheel 22 of the immunodiagnostic analyzer 20 to the waste container of the workstation 2 by the pick-and-place mechanism 56.

5. Loading of STAT Samples

Sample racks containing STAT samples for both the general chemical analyzer 10 and the immunodiagnostic analyzer 20 are treated in the same manner.

When there is no routine rack in the bypass area 34 of the workstation 20, the STAT rack will be placed onto the rack input area 32. The internal shuttle 40 will shuttle the STAT rack through the BCR 42 and to the cap-piercing station 52 and then to the sample pipette station 54. The control system will immediately interrupt the immunodiagnostic analyzer 20 to load the STAT aliquot, if any are available.

The STAT rack is then shuttled to the rack bypass area 34 of the workstation 2, from there it is shuttled by external shuttle 38 to the sample wheel 12 of the general chemical analyzer 10.

When there are routine racks in the bypass area 34 of the workstation 20, the STAT rack will also be placed onto the rack input area 32. The internal shuttle 40 will shuttle these routine racks back to the rack input area 32 to clear out the bypass area 34. The internal shuttle will then shuttle the STAT rack through the BCR 42, to the cap-piercing station 52, and then to the sample pipette station 54. The control system will immediately interrupt the immunodiagnostic analyzer 20 to load the STAT aliquot, if any are available.

The STAT rack is then shuttled to the rack bypass area 34 of the workstation 2, and from there it is shuttled by the external shuttle 38 to the sample wheel 12 of the general chemical analyzer 10.

6. Reflex Testing from the General Chemical Analyzer 10 to the Immunodiagnostic Analyzer 20

When a test performed by the general chemical analyzer 10 triggers or requires a reflex test by the immunodiagnostic analyzer 20, the rack containing the sample for which the reflex test is to be performed is shuttled back from the sample wheel 12 of the general chemical analyzer 10 to the rack input area 32 of the workstation 2 by the external shuttle 38 of the workstation 2.

The workstation 2 then routes the reflexed sample rack to the immunodiagnostic analyzer 20, utilizing the normal sample aliquoting and loading sequences, as described in Paragraphs 3 and 4 above. The control system of the workstation 2 will also communicate the reflex test information to the immunodiagnostic analyzer 20.

The above description of the functions and operations of workstation 2 of the present invention is provided for illustration purposes. With proper programming, these basic functions and operations may be combined, modified, and supplemented to perform various tasks required by the general chemical analyzer 10 and/or the immunodiagnostic analyzer 20.

The workstation of the present invention has many unique and advantageous features, including the integration of two or more automated chemical analyzers for performing a series of chemical analysis, the provision of a single common sample input area, and a single control console for the integrated automated chemical analyzers.

Additionally, the workstation of the present invention is capable of sampling from closed sample tubes and also capable of the rapid loading of STAT samples. Moreover, the workstation of the present invention is capable of facilitating automated reflex testing from one automated chemical analyzer to another.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An apparatus for integrating two or more automated analyzers, comprising a connector unit that is separate from said automated analyzers, wherein said connector unit comprises:
    a. a sample rack handler assembly, having a single common sample rack input area for loading sample racks for said two or more automated analyzers, and a sample rack bypass area for passing sample racks to be processed by one of said two or more automated analyzers, wherein the sample racks hold sample tubes containing samples;
    b. a sample aliquoting assembly, having an aliquot vessel storage tray holding aliquot vessels with and without the samples and a sample pipetter station for withdrawing the samples from the sample tubes and aliquoting the samples into the aliquot vessels for processing by one of said two or more automated analyzers;
    c. an internal shuttle for shuttling said sample racks between said sample rack input area, said sample rack bypass area, and said sample pipetter station;
    d. an external shuttle for shuttling said sample racks between said sample rack input area, said sample rack bypass area, and said one of said two or more automated analyzers; and
    e. means for randomly accessing and transporting said aliquot vessels between the aliquot vessel storage tray and one of said two or more automated analyzers.

2. The apparatus of claim 1, further comprising a single common control console for said workstation and said two or more automated analyzers.

3. The apparatus of claim 1, further comprising a bar code reader for ascertaining sample rack identification information.

4. The apparatus of claim 1, wherein said internal shuttle shuttles said sample racks to be sampled by said one of said two or more automated analyzers from said sample rank input area to said sample rack bypass area.

5. The apparatus of claim 4, wherein said internal shuttle also shuttles said sample racks to be aliquoted from said sample rack input area to said sample pipetter station.

6. The apparatus of claim 5, wherein said internal shuttle further shuttles sample racks from said sample pipetter station to said sample rack bypass area after sample aliquoting.

7. The apparatus of claim 1, further comprising a cap-piercing station for piercing caps of closed sample tubes contained in said sample racks.

8. The apparatus of claim 7, wherein said internal shuttle additionally shuttles sample racks between said sample rack input area, said sample rack bypass area, said cap-piercing station, and said sample pipetter station.

9. The apparatus of claim 1, wherein said external shuttle shuttles said sample racks to be processed by said one of said two or more automated analyzers from said sample rack bypass area to said one of said two or more automated analyzers.

10. The apparatus of claim 9, wherein said external shuttle also shuttles sample racks from said one of said two or more automated analyzers to said sample rack input area of said workstation for reflex testing by said other one of said two or more automated analyzers.

11. The apparatus of claim 1, further comprising a sample rack output area for off-loading sample racks after being processed by said one of said two or more automated analyzers.

12. The apparatus of claim 11, wherein said external shuttle further shuttles said sample racks from said one of said two or more automated analyzers back to said sample rack output area after being processed by said one of said two or more automated analyzers.

13. The apparatus of claim 1, wherein said transporting means is a pick-and-place mechanism.

14. An apparatus for integrating two automated analyzers, comprising a connector unit that is separate from said automated analyzers, wherein said connector unit comprises:
  a. a sample rack handler assembly, having a single common sample rack input area for loading sample racks for said two automated analyzers, wherein the sample racks hold sample tubes containing samples;
  b. said sample rack handler assembly also having a sample rack bypass area for passing sample racks to be processed by one of said two automated analyzers;
  c. said sample rack handler assembly, further having a sample rack output area for off-loading sample racks after being processed by said one of said two automated analyzers;
  d. a sample aliquoting assembly, having an aliquot vessel storage tray holding aliquoting vessels with and without the samples and a sample pipetter station for withdrawing the samples from the sample tubes and aliquoting the samples into the aliquot vessels for processing by one of said two automated analyzers;
  e. an internal shuttle for shuttling said sample racks to be processed by said one of said two automated analyzers from said sample rack input area to said sample rack bypass area, and also for shuttling said sample racks to be aliquoted from said sample rack input area to said sample pipetter station;
  f. an external shuttle for shuttling said sample racks to be processed by said one of said two automated analyzers from said sample rack bypass area to said one of said two automated analyzers, and also for shuttling said sample racks from said one of said two automated analyzers back to said sample rack output area after being processed by said one of said two automated analyzers; and
  g. a pick-and-place mechanism for transporting said aliquot vessels containing the samples between said aliquot vessel storage tray and one of said two automated analyzers.

15. The apparatus of claim 14, further comprising a single common control console for said workstation and said two automated analyzers.

16. The apparatus of claim 14, further comprising a bar code reader for ascertaining sample rack identification information.

17. The apparatus of claim 14, wherein said internal shuttle also shuttles sample racks from said sample pipetter station to said sample rack bypass area after sample aliquoting.

18. The apparatus of claim 14, further comprising a cap-piercing station for piercing caps of closed sample tubes contained in said sample racks.

19. The apparatus of claim 18, wherein said internal shuttle further shuttles sample racks between said sample rack input area, said sample rack bypass area, said cap-piercing station, and said sample pipetter station.

20. The apparatus of claim 14, wherein said external shuttle also shuttles sample racks from said one of said two automated analyzers to said sample rack input area of said workstation for reflex testing by said other one of said two automated analyzers.

21. An apparatus for integrating an automated general chemical analyzer and an automated immunodiagnostic analyzer, comprising a connector unit that is separate from said automated analyzers, wherein said connector unit comprises:
  a. a sample rack handler assembly, having a single common sample rack input area for loading sample racks for said automated general chemical analyzer and said automated immunodiagnostic analyzer, wherein the sample racks hold sample tubes containing samples;
  b. said sample rack handler assembly also having a sample rack bypass area for passing sample racks to be processed by said automated general chemical analyzer;
  c. said sample rack handler assembly, further having a sample rack output area or off-loading sample racks after being processed by said automated general chemical analyzer;
  d. a sample aliquoting assembly, having a cap-piercing station for piercing caps of closed sample tubes contained in said sample racks;
  e. said sample aliquoting assembly also having an aliquot vessel storage tray holding a aliquot vessels with and without the samples and a sample pipetter station for withdrawing the samples from the sample tubes and aliquoting the samples into the aliquot vessels for processing by said automated immunodiagnostic analyzer;
  f. an internal shuttle for shuttling said sample racks to be processed by said automated general chemical analyzer from said sample rack input area to said sample rack bypass area, and also for shuttling said sample racks to be aliquoted from said sample rack input area to said sample pipetter station;

g. an external shuttle for shuttling said sample racks to be processed by said automated general chemical analyzer from said sample rack bypass area to said automated general chemical analyzer, and also for shutting said sample racks from said automated general chemical analyzer back to said sample rack output area after being processed by said automated general chemical analyzer; and h. a pick-and-place mechanism for transporting said aliquot vessels containing the samples between said aliquot vessel storage tray and said automated immunodiagnostic analyzer.

22. The apparatus of claim 21, further comprising a single common control console for said workstation, said automated general chemical analyzer, and said automated immunodiagnostic analyzer.

23. The apparatus of claim 21, further comprising a bar code reader for ascertaining sample rack identification information.

24. The apparatus of claim 21 wherein said internal shuttle also shuttles sample racks from said sample pipetter station to said sample rack bypass area after sample aliquoting.

25. The apparatus of claim 21 wherein said internal shuttle further shuttles sample racks between said sample rack input area, said sample rack bypass area, said cap piercing station, and said sample pipetter station.

26. The apparatus of claim 21, wherein said external shuttle further shuttles sample racks from said automated general chemical analyzer to said sample rack input area of said workstation for reflex testing by said automated immunodiagnostic analyzer.

* * * * *